US007784943B2

(12) United States Patent
Adachi et al.

(10) Patent No.: US 7,784,943 B2
(45) Date of Patent: Aug. 31, 2010

(54) EYELID DETECTING APPARATUS, EYELID DETECTING METHOD AND PROGRAM THEREOF

(75) Inventors: Jun Adachi, Obu (JP); Tadashi Asano, Gifu (JP); Kenichi Ohue, Toyota (JP); Yuji Ninagawa, Aichi-ken (JP); Shinichi Kojima, Nisshin (JP)

(73) Assignee: Aisin Seiki Kabushiki Kaisha, Aichi-ken (JP)

( * ) Notice: Subject to any disclaimer, the term of this patent is extended or adjusted under 35 U.S.C. 154(b) by 191 days.

(21) Appl. No.: 11/962,350

(22) Filed: Dec. 21, 2007

(65) Prior Publication Data

US 2008/0151186 A1 Jun. 26, 2008

(30) Foreign Application Priority Data

Dec. 26, 2006 (JP) ............................ 2006-349031

(51) Int. Cl.
*A61B 3/14* (2006.01)

(52) U.S. Cl. ...................................................... 351/206

(58) Field of Classification Search ................. 351/205, 351/206, 209, 210, 211, 212; 382/117, 167, 382/165, 275, 164, 103, 274, 118, 199, 173, 382/162, 190, 115

See application file for complete search history.

(56) References Cited

U.S. PATENT DOCUMENTS 5,859,921 A * 1/1999 Suzuki ....................... 382/118
2004/0233299 A1* 11/2004 Ioffe et al. .................. 348/239
2004/0240747 A1* 12/2004 Jarman et al. ............... 382/274
2005/0220346 A1* 10/2005 Akahori ...................... 382/190
2006/0045317 A1 3/2006 Adachi et al.

FOREIGN PATENT DOCUMENTS

JP 03-2020245 A 9/1991
JP 07-181012 A 7/1995
JP 07-313459 A 12/1995

(Continued)

OTHER PUBLICATIONS

Japanese Office Action issued in JP 2007-071524 dated Jan. 20, 2009 (10 pages).

(Continued)

*Primary Examiner*—Timothy J Thompson
*Assistant Examiner*—Tuyen Q Tra
(74) *Attorney, Agent, or Firm*—Sughrue Mion, PLLC

(57) ABSTRACT

An eyelid detecting apparatus includes an image capturing portion for capturing a face image, a red-eye effect detecting portion for detecting a red-eye effect in which a light appears red at the pupil in the face image, the light entering through the pupil, reflecting on a choroidea of the eye, and exiting from the pupil, an eyelid detecting portion for detecting an upper eyelid and a lower eyelid in the face image on the basis of an edge appearing on a boundary between a bright portion and a dark portion and the eyelid detecting portion ignoring the edge of a red-eye effect occurring pupil so as not to be considered as the upper eyelid and the lower eyelid when the red-eye effect detecting portion detects the red-eye effect.

12 Claims, 15 Drawing Sheets

FOREIGN PATENT DOCUMENTS

| | | | |
|---|---|---|---|
| JP | 8-101915 | A | 4/1996 |
| JP | 10-044824 | A | 2/1998 |
| JP | 10-63850 | A | 3/1998 |
| JP | 11-066320 | A | 3/1999 |
| JP | 2000-067225 | A | 3/2000 |
| JP | 2000-123188 | A | 4/2000 |
| JP | 2000-137792 | A | 5/2000 |
| JP | 2001-137792 | A | 5/2000 |
| JP | 2000-339457 | A | 12/2000 |
| JP | 3143819 | B2 | 1/2001 |
| JP | 2001-307076 | A | 11/2001 |
| JP | 3444115 | B2 | 6/2003 |
| JP | 2005-25568 | A | 1/2005 |
| JP | 3312562 | B2 | 5/2005 |
| JP | 2005-29634 | A | 10/2005 |
| JP | 2006-065673 | A | 3/2006 |

OTHER PUBLICATIONS

Japanese Office Action issued in JP 2007-063149 dated Feb. 3, 2009 (14 pages).

International Search Report issued in PCT/JP2007/073311 dated Dec. 25, 2007 (3 pages).

Song, Xinguang, "Extraction of Facial Organ Features Using Partial Feature Template and Global Constraints," The IEICE Transactions of Institute of Information and Communication Engineers, Aug. 25, 1994, J77-D- II No. 8, pp. 1601-1609.

* cited by examiner

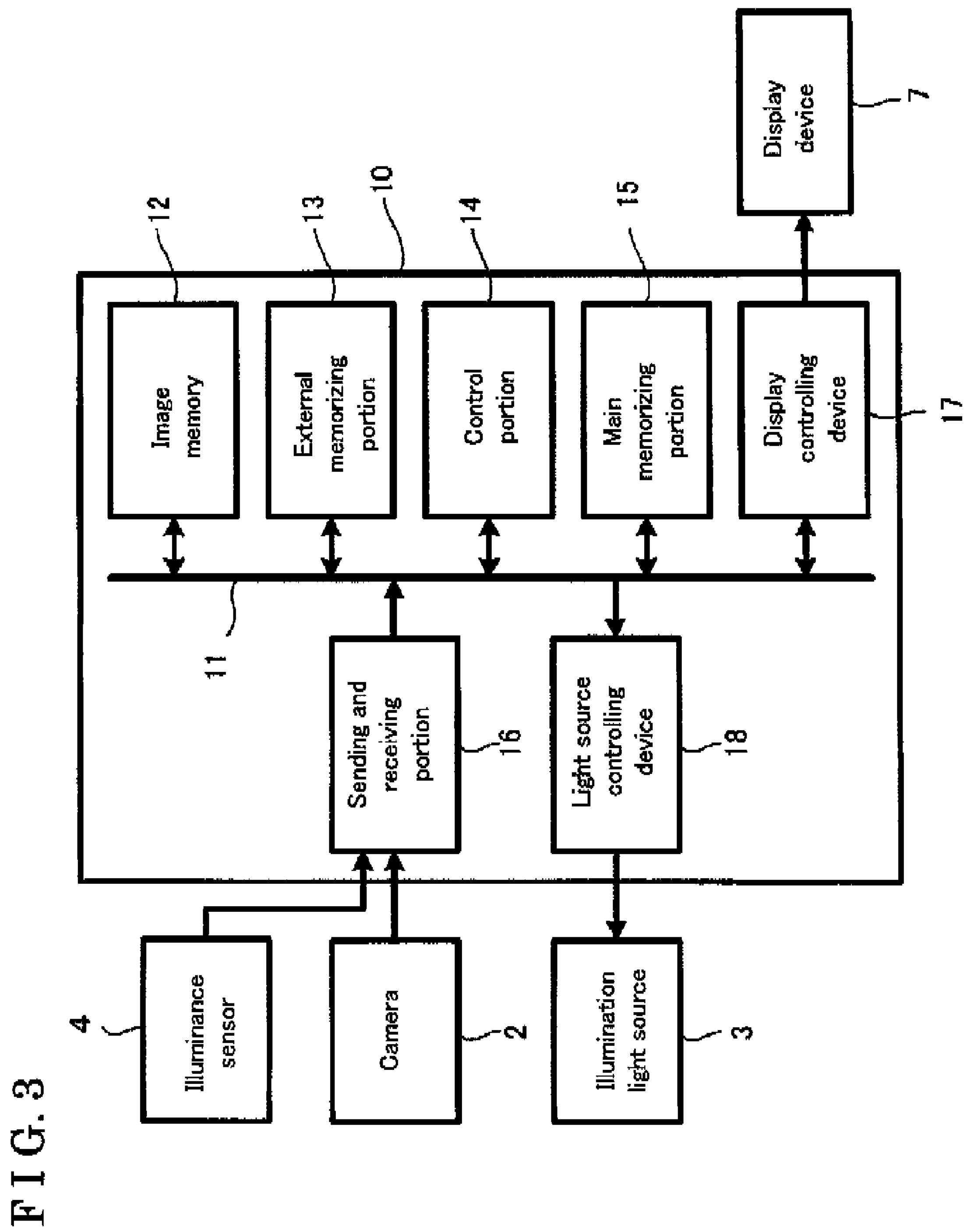
F I G. 3
Image memory
External memorizing portion
Control portion
Main memorizing portion
Display controlling device
Display device
Sending and receiving portion
Light source controlling device
Illuminance sensor
Camera
Illumination light source
12
13
10
14
15
7
17
11
16
18
4
2
3

FIG. 4A

Operator for detecting vertical edge

| | | |
|---|---|---|
| −1 | 0 | 1 |
| −2 | 0 | 2 |
| −1 | 0 | 1 |

FIG. 4B

Operator for detecting lateral edge

| | | |
|---|---|---|
| −1 | −2 | −1 |
| 0 | 0 | 0 |
| 1 | 2 | 1 |

F I G. 8 A
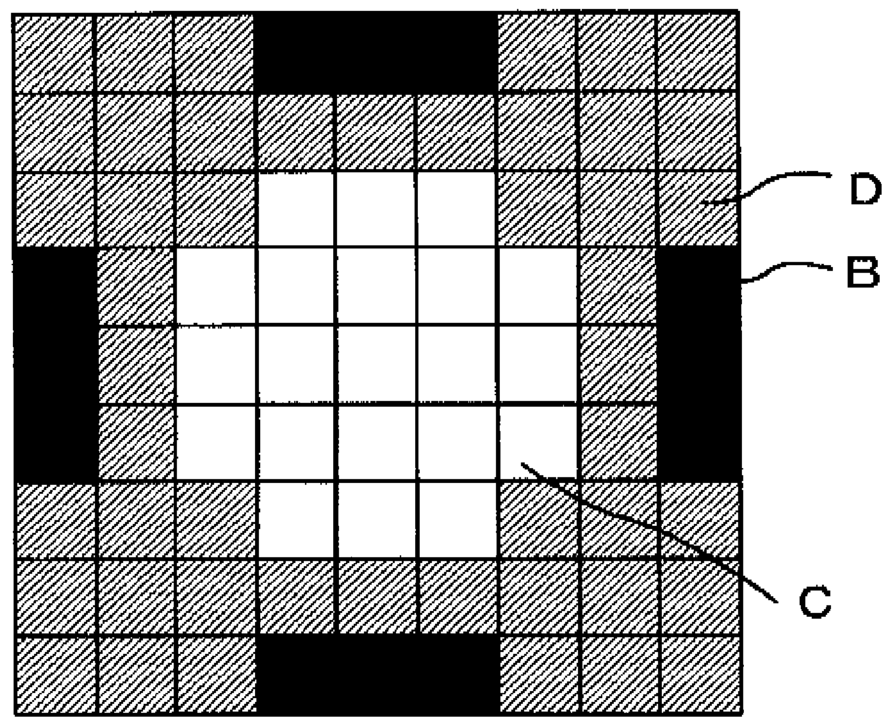
F I G. 8 B
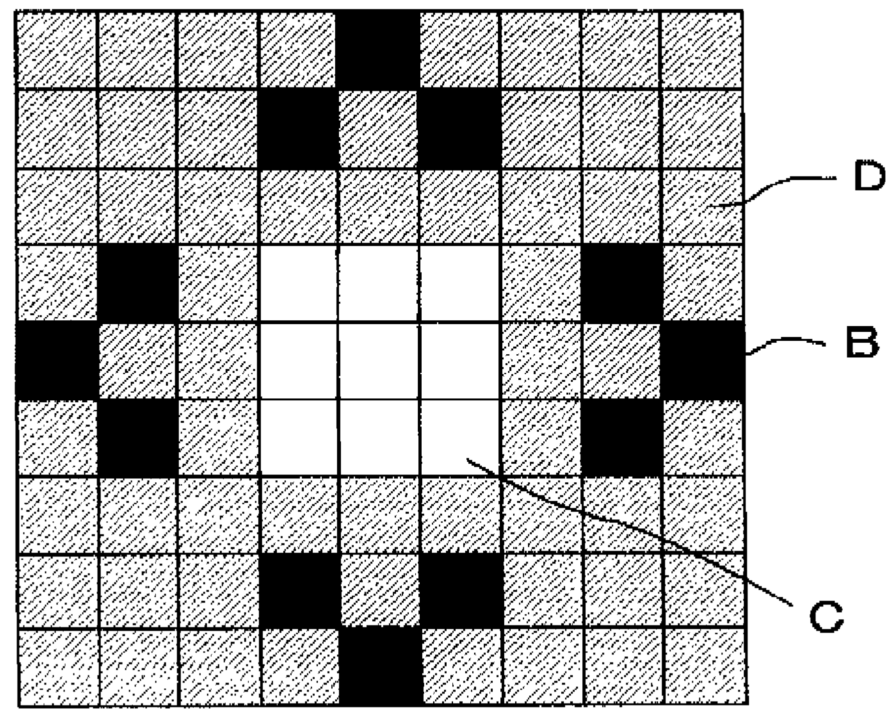

F I G. 12 B
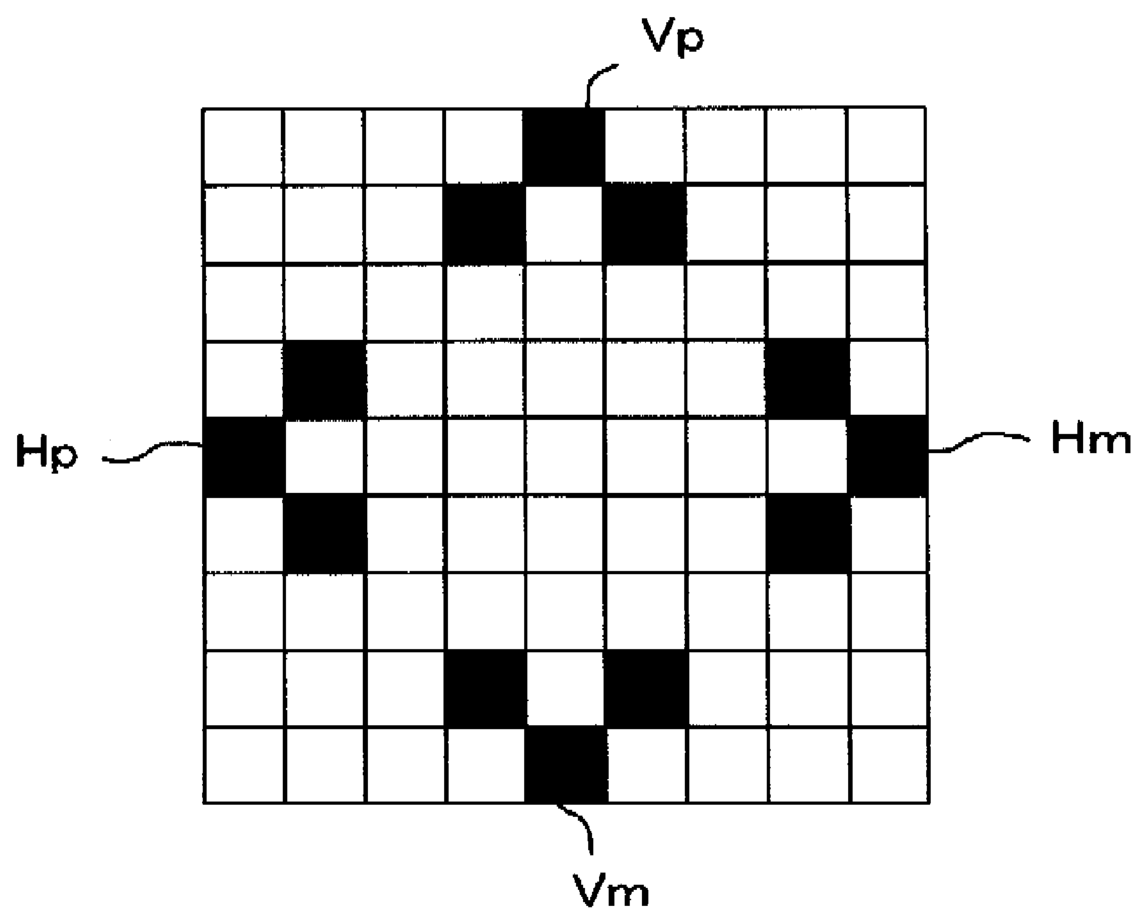

EYELID DETECTING APPARATUS, EYELID DETECTING METHOD AND PROGRAM THEREOF

CROSS REFERENCE TO RELATED APPLICATIONS

This application is based on and claims priority under 35 U.S.C. §119 to Japanese Patent Application 2006-349031 filed on Dec. 26, 2006, the entire content of which is incorporated herein by reference.

FIELD OF THE INVENTION

The present invention relates to an eyelid detecting apparatus, an eyelid detecting method and a program thereof, for detecting an upper eyelid and a lower eyelid in an image of the human face.

BACKGROUND

According to a known method related to an eyelid detection using a face image, a state of the eyes in the face image is determined, and a direction of a visual line of a human is measured on the basis of the state of the eyes, or an awakened level of a human, for example, a driver's awakened level, is estimated on the basis of an opening level of the driver's eyelids. In this method, the eyes need to be accurately detected in the face image in order to determine their state, and the eyelids need to be accurately detected in order to detect the opening level of the eyelids.

For example, according to a device disclosed in JP03202045, a driver's state is determined by detecting an iris portion in a face image. Specifically, an area in which the iris portion is searched is firstly set in the face image, and in this searching area, a size of the area in which a color is relatively dark is calculated, and a central position of the iris portion is detected by weighing possible central points of the iris portion through a statistical procedure depending on the size of the dark area.

Generally, when a human is shown in a picture, eyes of the human may appear red as a result of a red-eye effect. The red-eye effect generally occurs as follows. When the human is positioned in a poorly lighted environment, light enters through his/her pupils, which are wide opened in the poorly lighted environment. The light reflects on choroideas of the eyes and exits through the pupils, and then the camera captures this reflected light which has now passed twice tough the pupils. When the human is illuminated with a flash, the light of the flash passes too fast for the irises of his/her eyes to close the pupils, as a result, the red-eye effect occurs in the picture. When a subject is illuminated with the flash for a certain moment, because the pupils are is diminished in size during that moment, the red-eye effect may not occur.

Further, when the driver's face is captured by the camera in the poorly lighted environment and when illuminated by means of the flash, because the flash illuminates with visible light the flash may disturb the driver. As another option, the driver's face may be illuminated with a near-infrared light. However, when the near-infrared light passes through the pupils of the driver, because the pupils are not diminished in size, the red-eye effect occurs continuously.

According to the known art, in the face image where the red-eye effect occurs, because the pupils are determined as a bright area, an iris of the eye, which usually exists in a dark area in the image, may not be appropriately detected. Further, when the pupils are detected in the image where the red-eye effect occurs, an edge of the pupils may be mistakenly detected as an edge of the eyelids.

A need exists for an eyelid detecting apparatus, an eyelid detecting method and a program thereof which is not susceptible to the drawback mentioned above.

SUMMARY OF THE INVENTION

According to an aspect of the present invention, an eyelid detecting apparatus includes an image capturing portion for capturing a face image, a red-eye effect detecting portion for detecting a red-eye effect in which a light appears red at the pupil in the face image, the light entering through the pupil, reflecting on a choroidea of the eye, and exiting from the pupil, an eyelid detecting portion for detecting an upper eyelid and a lower eyelid in the face image on the basis of an edge appearing on a boundary between a bright portion and a dark portion and the eyelid detecting portion ignoring the edge of a red-eye effect occurring pupil so as not to be considered as the upper eyelid and the lower eyelid when the red-eye effect detecting portion detects the red-eye effect.

According to an aspect of the present invention, an eyelid detecting apparatus includes steps of detecting a red-eye effect in which a light appears red at the pupil in the face image, the light entering through the pupil, reflecting on a choroidea of the eye, and exiting from the pupil, detecting an upper eyelid and a lower eyelid in the face image on the basis of an edge appearing on a boundary between a bright portion and a dark portion and ignoring the edge of a red-eye effect occurring pupil so as not to be considered as the upper eyelid and the lower eyelid when the red-eye effect detecting portion detects the red-eye effect.

According to a aspect of the present invention, a program instructs a computer to function as a red-eye effect detecting portion for detecting a red-eye effect in which a light appears red at the pupil in a face image, the light entering through the pupil, reflecting on a choroidea of the eye, and exiting from the pupil and an eyelid detecting portion for detecting an upper eyelid and a lower eyelid in the face image on the basis of an edge appearing on a boundary between a bright portion and a dark portion in a manner where the edge of a red-eye effect occurring pupil is ignored so as not to be considered as the upper eyelid and the lower eyelid when the red-eye effect detecting portion detects the red-eye effect.

BRIEF DESCRIPTION OF THE DRAWINGS

The foregoing and additional features and characteristics of the present invention will become more apparent from the following detailed description considered with reference to the accompanying drawings, wherein:

FIG. 3 illustrates a block diagram indicating a configuration of a computer illustrated in FIG. 1;

FIG. 4A illustrates a diagram indicating an example of an operator for detecting vertical edge;

FIG. 4B illustrates a diagram indicating an example of an operator for detecting lateral edge;

FIG. 5C illustrates a diagram indicating an example of the dark-bright pixel pattern for detecting the red-eye effect;

FIG. 5D illustrates a diagram indicating an example of the dark-bright pixel pattern for detecting the red-eye effect;

FIG. 12B illustrates an example of the edge pattern for detecting the red-eye effect;

DETAILED DESCRIPTION

Figure 1:
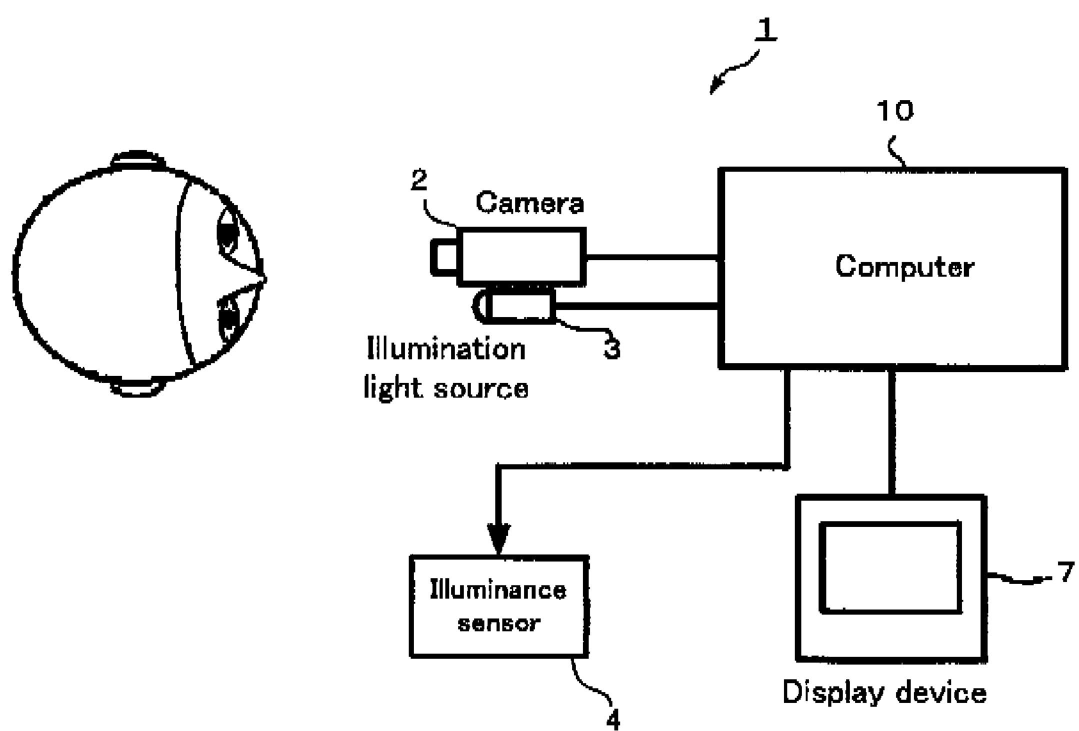
FIG. 1 illustrates a block diagram indicating an eyelid detecting apparatus related to the embodiment of the present invention.

An embodiment of the present invention will be described in detail in accordance with the attached drawings. Referring to the drawings, identical reference numeral designations may indicate the same or corresponding parts trough several views, and detailed description of the identical reference numeral designations will not repeated. FIG. 1 is a block diagram illustrating a configuration of an eyelid detecting apparatus 1 related to the embodiment of the present invention. The eyelid detecting apparatus 1 includes a camera 2 (e.g., an image capturing means), an illumination light source 3, an illuminance sensor 4 (e.g., an illuminance detecting means), a computer 10 and a display device 7. Specifically, the camera 2 captures an image of a driver's face and then produces a face image. The illumination light source 3 illuminates the driver's face. The computer 10 determines eyes of the driver. The display device 7 is connected to the computer 10.

The camera 20 converts an image formed by a lens into an electric signal by using, for example, a Charge Coupled Device (CCD), and then the camera 2 outputs an image data each of whose picture elements is digitalized. Further, the camera 2 produces, for example, a grayscale image of the face of the driver. The image data produced by the camera 2 includes not only the driver's face but also a background image behind the driver.

The illuminance sensor 4 includes, for example, a photodiode or a photoelectric conversion element such as a solar cell. The illuminance sensor 4 detects a level of brightness of surroundings by converting the light corresponding to an element into voltage or an electric current. The illuminance sensor 4 is provided at a place at which, for example, the level of brightness of the surroundings of the vehicle can be detected.

The display device 7 is configured with, for example, a Liquid Crystal Display (LCD), a Cathode Ray Tube (CRT) and lie like. Further, the display device 7 displays, for example, a binary image that is created on the basis of the face image captured by the camera 2.

The computer 10 processes the image data produced by the camera 2, and then the computer 10 determines right and left ends of the driver's face in a width direction thereof in the face image, and further, the computer 10 determines upper and lower portions of the driver's face in a vertical direction in the face image. The computer 10 sets an area (an eyelid searching area) to be searched in order to detect the eyelids of the drivers, and then the computer 10 determines a red-eye effect and upper and lower eyelids in the driver's face within the eyelid searching area set in the face image.

Figure 2:
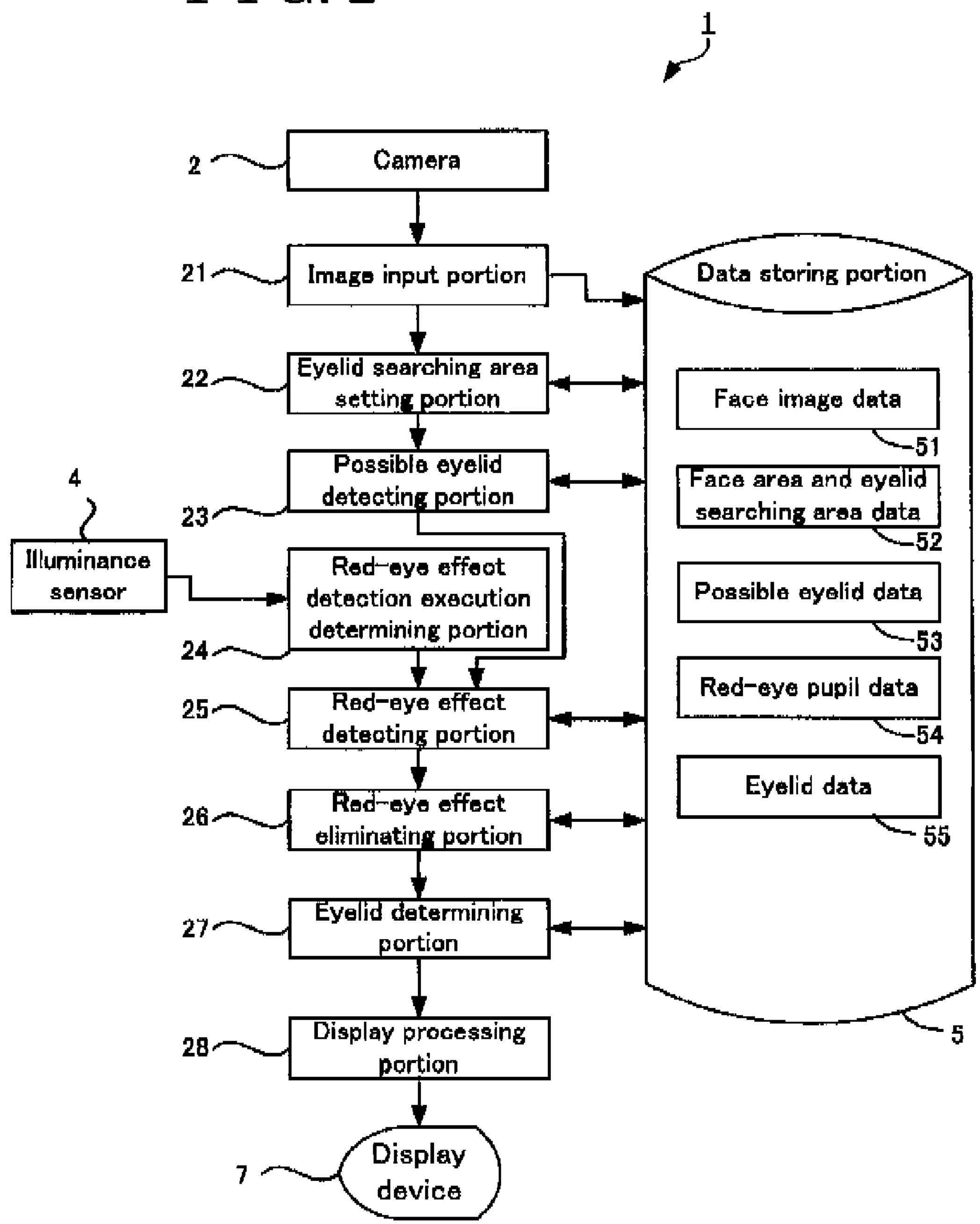
FIG. 2 illustrates a block diagram indicating a logical configuration of the eyelid detecting apparatus related to the embodiment of the present invention.

FIG. 2 is a block diagram illustrating a logical configuration of the eyelid detecting apparatus 1 of the embodiment. The eyelid detecting apparatus 1 includes the camera 2, the illuminance sensor 4, an image input portion 21, an eyelid searching area setting portion 22, a possible eyelid detecting portion 23 (e.g., a possible eyelid detecting means, an eyelid detecting means), a red-eye effect detection execution determining portion 24 (e.g., a red-eye effect detection execution determining means), a red-eye effect detecting portion 25 (e.g., a red-eye effect detecting means), a red-eye effect eliminating portion 26 (e.g., the eyelid detecting means), an eyelid determining portion 27 (e.g., the eyelid detecting means), a display processing portion 28, a data storing portion 5, a display device 7 and the like. The data storing portion 5 stores face image data 51, face area and eyelid searching area data 52, possible eyelid data 53, red-eye effect occurring pupil data 54, eyelid detection data 55. In this configuration, the eyelid detecting apparatus 1 determines the red-eye effect and two pairs of the upper and the lower eyelids of the eyes in the face image.

FIG. 3 is a block diagram illustrating an example of a configuration of the eyelid detecting apparatus 1. The computer 10 includes a sending and receiving portion 16 (e.g., the image capturing means), an image memory 12, an external memorizing portion 13, a control portion 14, a main memorizing portion 15, a display controlling device 17, and a light source controlling device IS. Each of the image memory 12, the external memorizing portion 13, the main memorizing portion 15, the sending and receiving portion 16, the display controlling device 17 and the light source controlling device 18 is connected to the control portion 14 via an internal bus 11. The control portion 14 serves as the image capturing means, the red-eye effect detection execution determining means, the red-eye effect detecting means and the eyelid detecting means.

The control portion 14 is configured with a Central Processing Unit (hereinafter referred to as a CPU) and the like. The control portion 14 follows a program memorized in the external memorizing portion 13 in order to execute processes of the image input portion 21, the eyelid searching area setting portion 22, the possible eyelid detecting portion 23, the red-eye effect detection execution determining portion 24, the red-eye effect detecting portion 25, the red-eye effect eliminating portion 26, the eyelid deter portion 27 and the display processing portion 28. The signal processes required in the image input portion 21, the eyelid searching area setting portion 22, the possible eyelid detecting portion 23, the red-eye effect detection execution determining portion 24, the red-eye effect detecting portion 25, the red-eye effect eliminating portion 26, the eyelid determining portion 27 and the display processing portion 28 are executed by the control portion 14 and the programs executed by the control portion 14.

The main memorizing portion 15 is configured with a Random-Access Memory (RAM) and the like. Further, the main memorizing portion 15 is utilized as a working area of the control portion 14. A part of the image memory 12 and a part of the main memorizing portion 15 are assigned to the data storing portion 15 as memory areas.

The external memorizing portion 13 is configured with nonvolatile memories, such as a flash memory, a hard disk, a Digital Versatile Disc (DVD), a Digital Versatile Disc Random-Access Memory (DVD-RAM), a Digital Versatile Disc ReWritable (DVD-RW) or the like. The external memorizing portion 13 preliminarily memorizes a program for executing the above-mentioned processes at the control portion 14. Further, the control portion 14 executes the program following the program data memorized in the external memorizing portion 14. Then, the external memorizing portion 13 memorizes a data sent from the control portion 14. For examples time-series image data may be stored at the external memorizing portion 13.

When a network is utilized for the eyelid detecting apparatus 1, the sending and receiving portion 16 is configured with, for example, either one of a Modulator-demodulator or a network terminator and either one of a serial interface or a Local Area Network interface (LAN interface) that is connected to the either one of the Modulator-demodulator or the network terminator. On the other hand, when the camera 2 is directly connected to the computer 10, the sending and receiving portion 16 is configured with, for example, a National Television Standard Committee interface (NTSC interface). The control portion 14 inputs the image data from the camera 2 via the sending and receiving portion 16. The image memory 12 memorizes the image data that is produced by means of the camera 2 and that is inputted to the image memory 12 via the sending and receiving portion 16. When the sending and receiving portion 16 is configured with the NTSC interface, image signals is converted into digital data by the sending and receiving portion 16. The sending and receiving portion 16 further inputs a signal corresponding to illuminance of the surroundings (brightness of the surroundings) from the illuminance sensor 4, and the signal is transmitted to the controlling portion 14.

The display controlling device 17 controls the display device 7 under the control of the control portion 14. The light source controlling device 18 controls the illumination light source 3 to be turned on or turned off.

The control portion 14 executes the program stored in the external memorizing portion 13 in order to detect a pair of the upper and lower eyelids. Specifically, the control portion 14 detects the pair of the upper and lower eyelids by executing the programs stored in the external memorizing portion 13 in a manner where, firstly the control portion 14 processes the image data produced by the camera 2, secondly the control portion 14 detects the right and the left ends and the upper and the lower portions of the face, thirdly the control portion 14 detects the red-eye effect and the possible upper and the lower eyelids within the eyelid searching area on the basis of the detected right and the left ends and the detected upper and the lower portions of the face, and then finally, the control portion 14 selects the best as the upper and the lower eyelids pairs Tom within a possible upper and lower eyelids pair that suit to a condition of the upper and the lower eyelids.

Returning to FIG. 2, an operation of each portion of the eyelid detecting apparatus 1 will be described below. The camera 2 captures the image of the face. The image input portion 21 inputs the time-series image data from the camera 2 at every predetermined time interval, and then the image input portion 21 outputs the inputted time-series image to the data storing portion 5. Then the data storing portion 5 memorizes the time-series image as the face image data 51.

Figure 5:
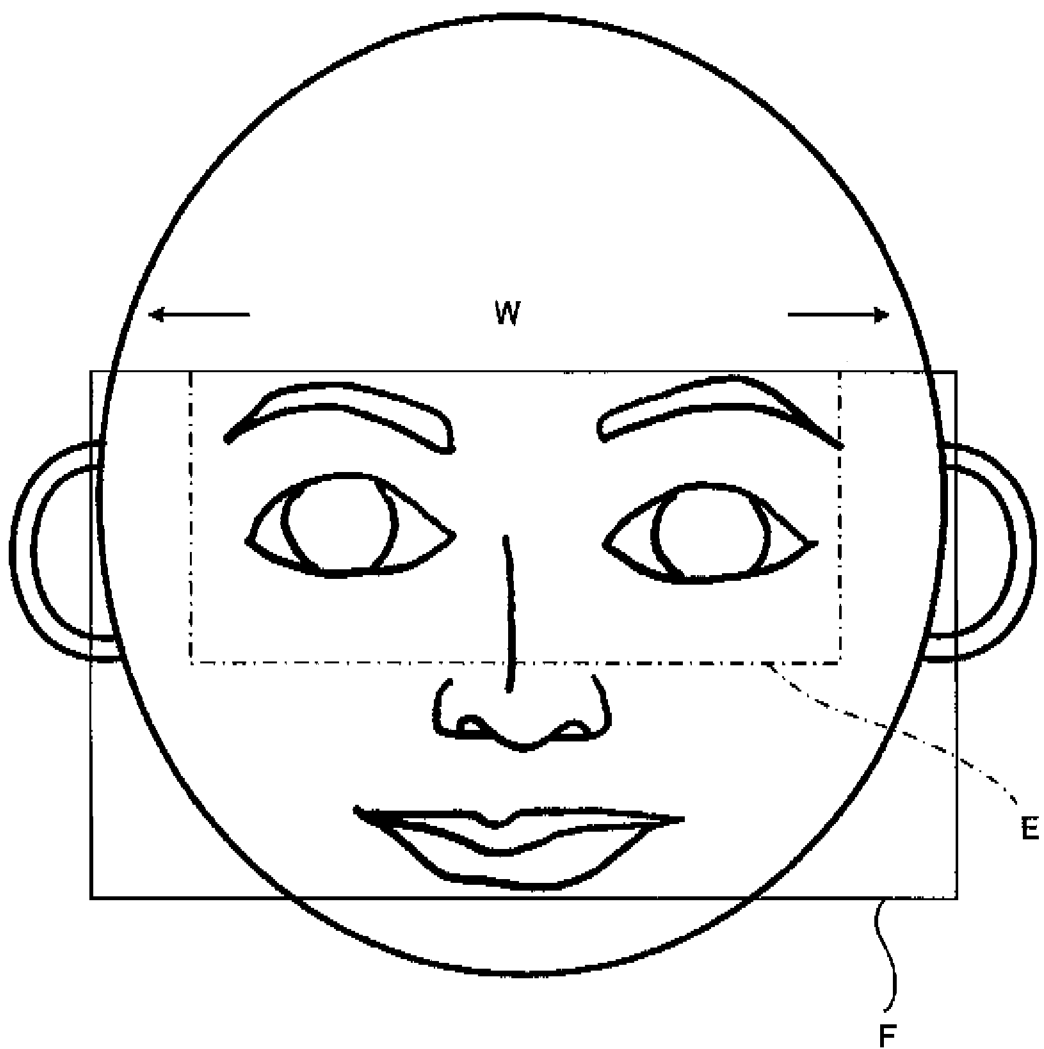
FIG. 5 illustrates a diagram indicating an example of data specifying areas in a face image.

The eyelid searching area setting portion 22 abstracts the face area from the face image data 51, and then the eyelid searching area setting portion 22 sets the eyelid searching area within the face area. In order to abstract the face area, for example, edges forming an outline of the face are abstracted from the face image. Alternatively, the outline of the face may be abstracted by means of a pattern matching method. The face area is set by detecting edges located above the eyebrows and an edge located below the chin within the face outline. Then, the eyelid searching area is set in the face area in a ratio obtained by statistical data. FIG. 5 illustrates an example of a face area F and an eyelid searching area E. The eyelid searching area setting portion 22 outputs the face area D and the eyelid searching area E to the storing portion 5, and the storing portion 5 memorizes the face area D and the eyelid searching area E as the face area and eyelid searching area data 52.

An eye-catching peculiar parts in the face image, for example nostrils, may be detected first, and the eyelid searching area E may be set on the basis of the positions of the nostrils. Specifically, a length between the nostrils and the eyebrow is measured, and the length is multiplied by a predetermined ratio. This length may be set as a vertical length of the eyelid searching area E. Further, a length of the width of the face line is measured, and the length is multiplied by a predetermined ratio. This length may be set as a horizontal length of the eyelid searching area E. By setting the eyelid searching area B in is manner, the eyelid detection may be improved more efficiently.

FIGS. 4A, 4B, 4C and 4D are diagrams for explaining an example of fixed data that is used for computing an edge. The external memorizing portion 13 stores an operator of the sobel filter for detecting horizontally changing edges and an operator for detecting vertically changing edges. In this embodiment, the concatenation of dots whose brightness change from bright to dark, or from dark to bright in a horizontal direction are referred to as horizontally changing edges. The dots of the horizontally changing edges generally continue in a vertical direction, hence, the horizontally changing edges are also referred to as vertical edges.

On the other hand, the concatenation of dots whose brightness change from bright to dark, or from dark to bright in a vertical direction are referred to as vertically changing edges. The dots of the vertically changing edges generally continue in a lateral direction, hence, the vertically changing edges are also referred to as lateral edges.

Figures 4C, 4D:
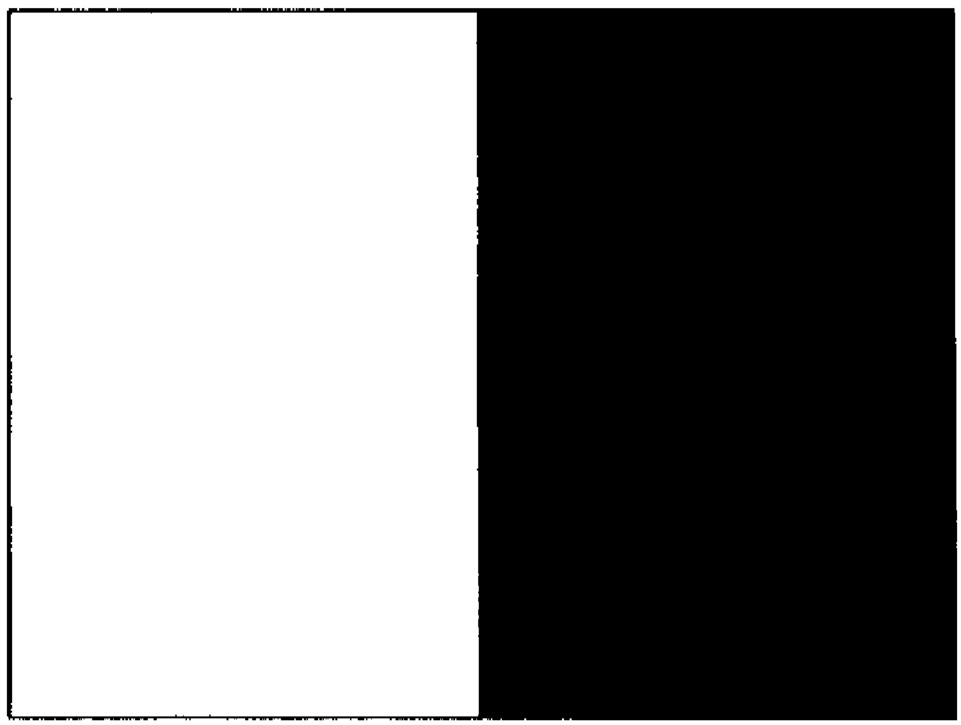
FIG. 4C illustrates a diagram indicating an example of a boundary (edge) between the dark color and the bright color that continue in the vertical direction.
FIG. 4D illustrates a diagram indicating an example of a boundary (edge) between the dark color and the bright color that continue in the lateral direction.

The sobel filter for detecting the horizontally changing edges (the vertical edges) illustrated in FIG. 4A is the operator for abstracting a boundary (edge) between dark color and bright color that continue in the vertical direction as illustrated in FIG. 4C. The sobel filter for detecting the vertically changing edges (the lateral edges) illustrated in FIG. 4B is the operator for abstracting a boundary (edge) between the dark color and the bright color that continue in the lateral direction as illustrated in FIG. 4D.

As illustrated in FIG. 5, the external memorizing portion 13 stores data specifying the face area F in the face image and data specifying the eyelid searching area E in the face image stored in the main memorizing portion 15. In the eyelid searching area E, eyes and eyebrows are assumed to exist.

Figure 6:
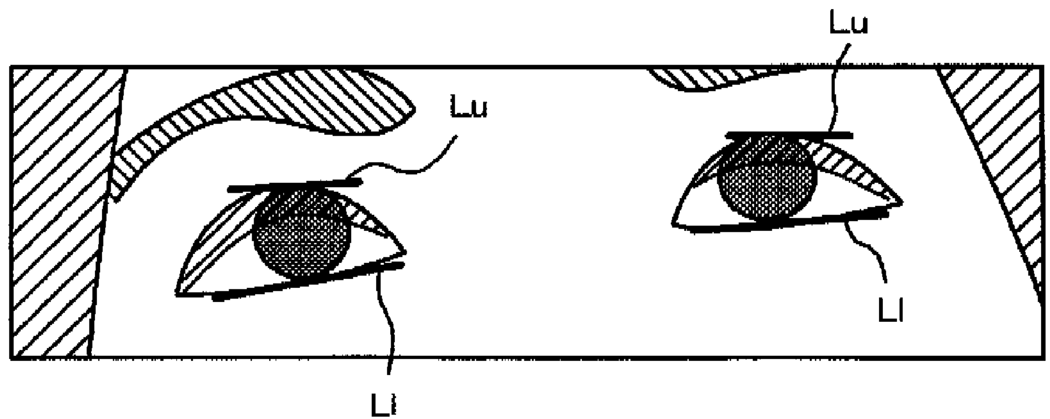
FIG. 6 illustrates a diagram indicating a pattern diagram indicating an example of an original image of an eyelid searching area.

The possible eyelid detecting portion 23 computes a horizontally changing edge and a vertically changing edge by use of, for example, filters illustrated in FIGS. 4A and 4B. FIG. 6 schematically illustrates an original image of the eyelid searching area E. In FIG. 6, hatching is applied to dark areas in the image, and positions of the vertically changing edges of the eyelids are illustrated by solid lines. Specifically, a position where the edge of the upper eyelid is detected is indicated with a solid line Lu, and a position where the edge of the lower eyelid is detected is indicated with a solid line L1. Further, edges of an eyebrow and the iris are also detected as the vertically changing edges.

Edges that change from bright to dark in a direction from top to bottom in the vertically changing edges are set as a possible upper eyelid, and edges that change from dark to bright in a direction from top to bottom in the vertically changing edges are set as possible lower eyelids. The possible eyelid detecting portion 23 sets the possible upper eyelids and the possible lower eyelids as the possible eyelid data 53, and the data is memorized in the data storing portion 5.

On the basis of a combination of the horizontally changing edges and the vertically changing edges, likelihood of the possible upper eyelid and the possible lower eyelid may be determined. For example, because the upper eyelid generally curves so as to project upwardly, horizontally changing edges may appear on both ends of the vertically changing edge. Thus, the vertically changing edge in which the horizontally changing edges exist is considered as the possible upper eyelid that is definite.

Figure 7:
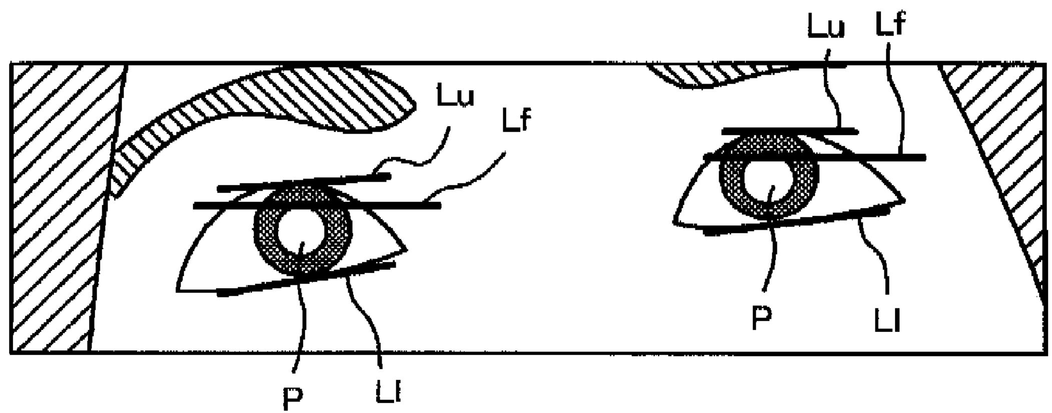
FIG. 7 illustrates a diagram indicating a pattern diagram indicating an example of an image in which a red-eye effect occurs.

FIG. 7 schematically illustrates an image of We eyelid searching area E where the red-eye effect occurs. In the same manner as the drawing illustrated in FIG. 6, hatching is applied to dark areas in the image. At the upper portion of the pupil P where the red-eye effect occurs (hereinbelow referred to as a red-eye effect occurring pupil), the brightness changes from dark to bright in a direction from top to bottom. Thus, a vertically changing edge, which changes from dark to bright in a direction from top to bottom in the same manner as the lower eyelid, exists. A solid line Lf illustrated in FIG. 7 indicates a position of the vertically changing edge calculated on the red-eye effect occurring pupil. At the lower portion of the pupil P, another vertically changing edge, which changes from dark to bright in a direction from top to bottom in the same manner as the upper eyelid, is calculated.

The vertically changing edge appearing in the red-eye effect occurring pupil P may be a possible upper eyelid and a possible lower eyelid. The possible upper eyelid or the possible lower eyelid in the red-eye effect occurring pupil P may be determined as an actual eyelid. Specifically, when the possible lower eyelid appearing at the upper portion of the red-eye effect occurring pupil P is determined as the lower eyelid, the control portion 14 may determine that the eye is closed on the basis of a positional relation between the possible lower eyelid and the possible upper eyelid.

A signal from the illuminance sensor 4, the signal corresponding to brightness of the surroundings of the driver is inputted to the red-eye effect detection execution determining portion 24. When the surroundings of the driver are bright, because the pupils of the driver's eyes diminish in size, the red-eye effect generally does not occur. On the other hand, when the surroundings of the driver are dark, the pupils of the driver's eyes are widely opened, so that the red eye effect generally occurs. The red-eye effect detection execution determining portion 24 outputs a command to detect the red-eye effect to the red-eye effect detecting portion 25 when the level of the brightness of the surroundings is lower than a predetermined level. On the other hand, when the level of the brightness of the surroundings is higher than the predetermined level, the red-eye effect detection execution determining portion 24 outputs a command not to detect the red-eye effect to the red-eye effect detecting portion 25.

The red-eye effect may be constantly detected without using the illuminance sensor 4 or the red-eye effect detection execution determining portion 24. According to the embodiment, the red-eye effect is selectively detected on the basis of the brightness of the surroundings, so that the eyelid detecting process is effectively detected in case where the red-eye effect does not occur in the bright surroundings.

The red-eye effect detecting portion 25 detects the pupil in which the red-eye effect occurs in the eyelid searching area E. In order to detect the pupil where the red-eye effect occurs, the red-eye effect occurring pupil P is determined by selecting a partial image in the face image that matches a predetermined dark-bright pixel pattern.

Figure 8C:
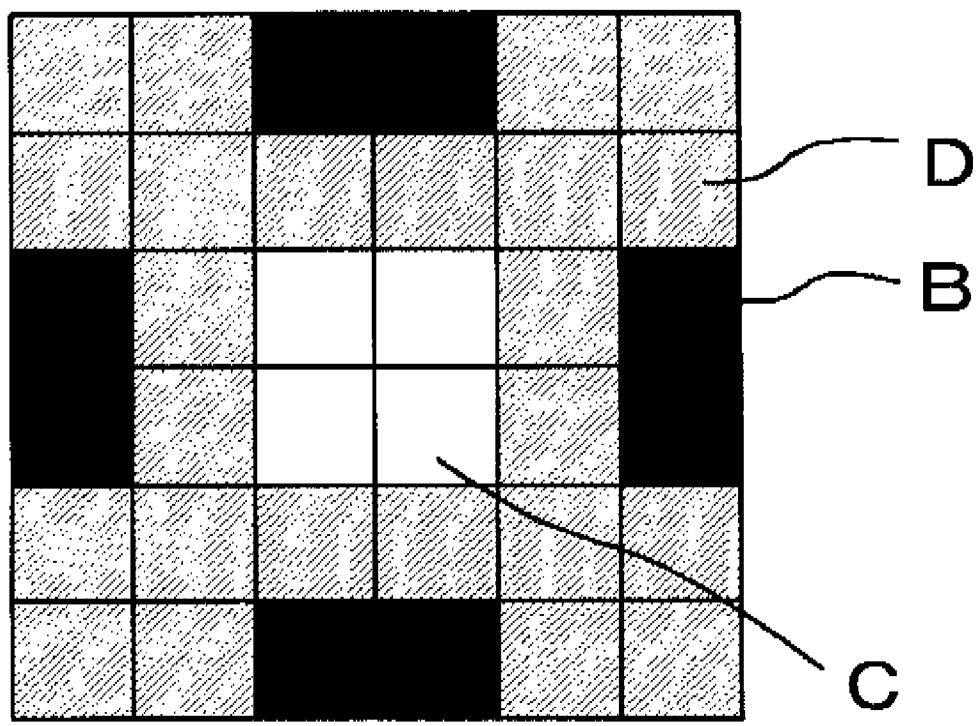
FIG. 8A illustrates a diagram indicating an example of a dark-bright pixel pattern for detecting the red-eye effect.
FIG. 8B illustrates a diagram indicating an example of the dark-bright pixel pattern for detecting the red-eye effect.
Figure 8D:
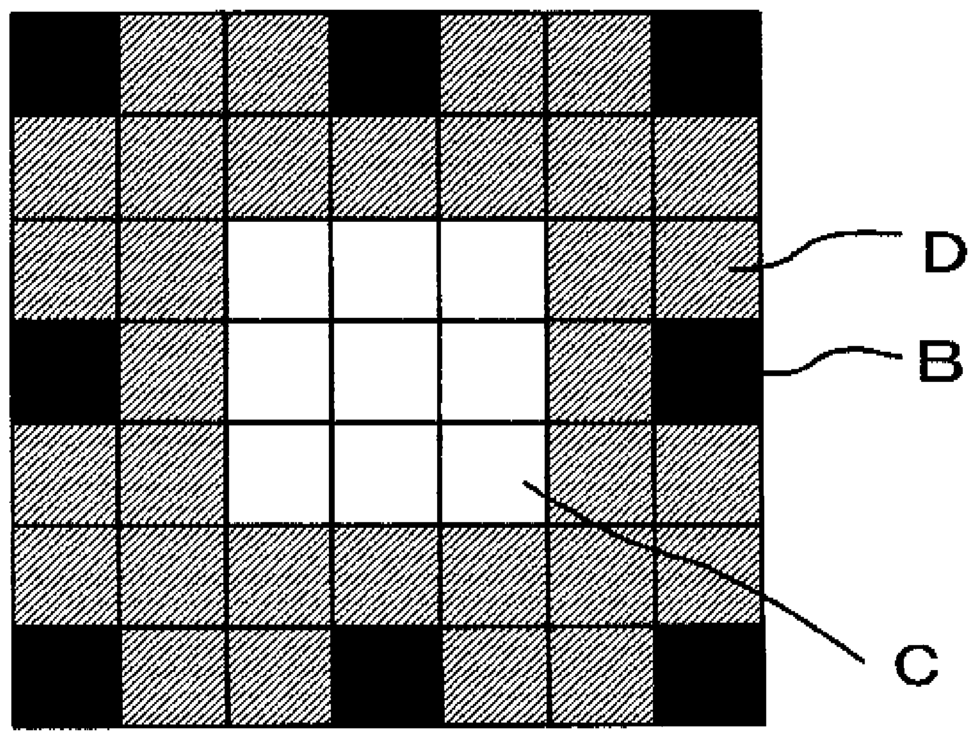

FIGS. 5A through 5D illustrates diagrams indicating examples of the dark-bright pixel pattern used for detecting red-eye effect occurring pupil. In each of FIGS. 8A through 8D, each small square indicates a pixel. Each FIGS. 8A and 8B illustrates a pixel a may of 9×9, FIG. 8C illustrates a pixel array of 6×6, and FIG. 8D illustrates a pixel away of 7×7.

In the drawings, each white square indicates a pixel whose brightness is equal to or more than a predetermined threshold value "a" (hereinbelow referred to as a white pixel C), and each black square indicates a pixel whose brightness is equal to or less than a predetermined threshold value "b" (hereinbelow referred to as a black pixel B). Each square to which a hatching is applied indicates a pixel (hereinbelow referred to as a not-considered pixel D) that is not considered when the face image is compared to the dark-bright pixel pattern. The threshold value "a" and the threshold value "b" are not the same value.

The dark-bright pixel pattern is overlapped on the face image, and partial images in the face image that are overlapped by the white pixel C and the black pixel B are examined. When each pixel of the partial image in the face image corresponds to a white and black pixel pattern in the dark-bright pixel pattern (logical product is all true), the control portion 4 determines that the partial image in the face image is identical to the dark-bright pixel pattern.

In this examination, the pixels in the face image corresponding to the not-considered pixels D in the dark-bright pixel pattern are not considered. Specifically, each pixel in the partial image in the face image that corresponds to the white pixel C of the dark-bright pixel pattern is examined whether or not the brightness thereof is equal to or more than the threshold value "a", and each pixel in the partial image in the face image that corresponds to the black pixel B of the dark-bright pixel pattern is examined whether or not the brightness thereof is equal to or less than the threshold value "b". When the partial image in the face image is determined so as to be identical to the dark-bright pixel pattern, the red-eye effect detecting portion 25 determines that the red-eye effect occurring pupil exists in the partial image in the face image. In his manner, a red-eye effect occurring pupil whose brightness changes in all directions within the two-dimensional image may be detected.

In each example of the dark-bright pixel patterns illustrated in FIGS. 8A through 8D, the white pixels C, which are also referred to as bright area, exist at the central portion of the pixel pattern, and the black pixels B, which are also referred to as dark area, exist around the white pixels C. Generally, when the red-eye effect occurs, the level of the brightness of the pupils increases, and the level of the brightness of the irises around the pupils decreases. In the light of this characteristic, the red-eye effect is detected by use of the dark-bright pixel patterns in which the bright area exist at the central portion, and the dark area exist around the central portion as illustrated in FIGS. 5A and 8D.

The dark-bright pixel pattern is set so as to fit the pupil where the red-eye effect occurs in consideration of the size of the face image and a resolution level of the camera.

For example, in an image whose resolution level is relatively high, the number of the bright pixels in the bright area (white pixels C) at the central portion of the image may be increased as illustrated in FIG. 8A. On the other hand, in an image whose resolution level is relatively low, the number of the bright pixels in the bright area (white pixels C) may be decreased as illustrated in FIG. 8C. In each pattern, the not-considered pixels D are provided between the bright pixels and the dark pixels in order to cope with the variations of the sizes of the bright and dark areas.

Further, plural dark-bright pixel patterns are prepared in advance, and the red-eye effect occurring pupils may be determined when the face image corresponds to any of the dark-bright pixel patterns. Thus, the level of the accuracy of the red-eye effect detection may be increased even when the face direction, or even when the size of the eye differs among individuals.

Other methods may be used in order to detect the red-eye effect. For example, the pupil where the red-eye effect occurs may be detected on the basis of the shape of a border line between the bright area and the dark area.

Figure 9:
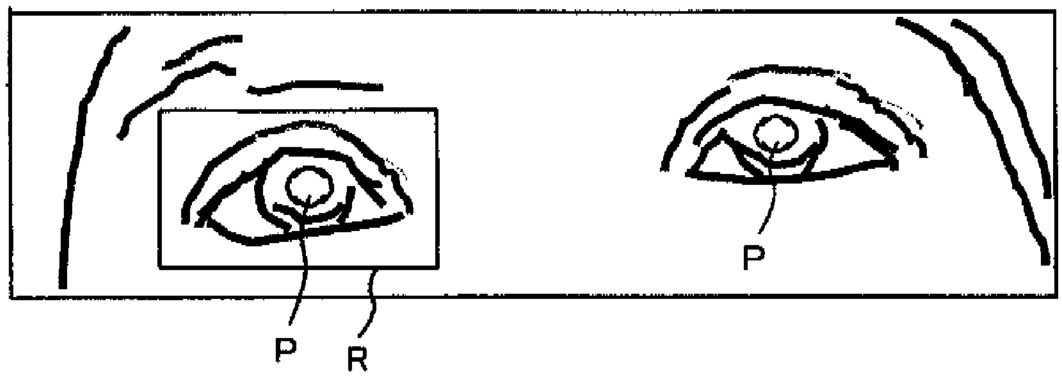
FIG. 9 illustrates a diagram indicating example where an edge is detected in an image of an eyelid searching area when the red-eye effect is detected.

FIG. 9 illustrates an example in which edges between the bright area and the dark area are detected in the image of the eyelid searching area E where the red-eye effect occurs. In this example, the pupil where the red-eye effect occurs appears as a bright area, and the iris existing around the pupil appears as a dark area, and a border between the bright area and the dark area appears around the red-eye effect occurring pupil P. The red-eye effect occurring pupil P is detected on the basis of a shape of the border. Specifically, when the shape of the border fulfills predetermined conditions, the edge is considered as the red-eye effect occurring pupil P. A detailed description of this method will be explained below.

Figure 10:
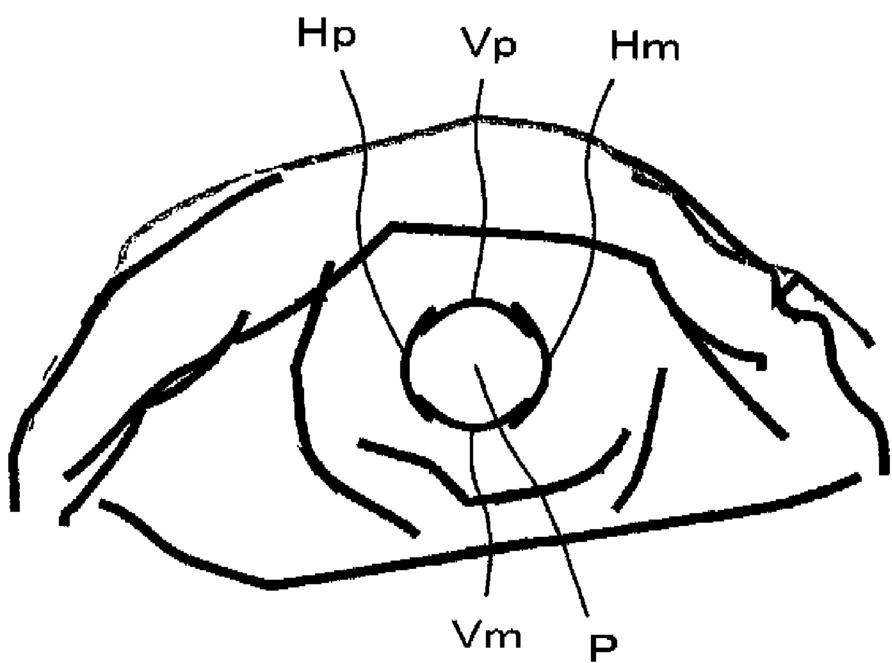
FIG. 10 illustrates an enlarged diagram indicating an area R in FIG. 9.

FIG. 10 illustrates a drawing indicating an enlarged view of an area R of FIG. 9. In the red-eye effect occurring pupil P, a horizontally changing edge, which changes from dark to bright in a left-to-right direction, appears at the left end of the red-eye effect occurring pupil P facing the face image. This edge is referred to as a plus vertical edge Hp. In addition, another horizontally changing edge, which changes from bright to dark in a left-to-right direction, appears at the right end of the pupil facing the face image. This edge is referred to as a minus vertical edge A. Further, a vertically changing edge, which changes from dark to bright in a direction from top to bottom, appears at the upper end of the red-eye effect occurring pupil P. This edge is referred to as a plus lateral edge Vp. Further, another vertically changing edge, which changes from bright to dark in a direction from top to bottom direction, appears at the lower end of the red-eye effect occurring pupil P. This edge is referred to as a minus lateral edge Vm.

When the range is being surrounded by the plus vertical edge Hm at the left, the minus vertical edge Hm at the right, the plus lateral edge Vp at the upper portion and the minus lateral edge Vm at the lower portion is determined as the red-eye effect occurring pupil P in the eyelid searching area E, and when this range includes predetermined number of pixels, such range is determined as the red-eye effect occurring pupil P. Thus, the eyelid searching area E is scanned in order to detect the red-eye effect occurring pupil P under those conditions.

Further, the red-eye effect occurring pupil P may be detected on the basis of a predetermined dark-bright edge pattern. FIGS. 12A through 12D indicate examples of the edge pattern for detecting the red-eye effect. A blackened area indicates each edge, specifically, the plus lateral edge Vp is located at the upper portion of the pattern, the minus lateral edge Vm is located at the bottom portion of the pattern, the plus vertical edge Hp is located at the left portion of the pattern and the minus vertical edge Hm is located at the right of the pattern. The pattern may include a point that may belong to both of the lateral edge and the vertical edge. For example, as illustrated in FIG. 12D, the pattern includes a common point K1 that belongs to both of the plus lateral edge Vp and the plus vertical edge Hp, a common point K2 that belongs to the plus lateral edge Vp and the minus vertical edge Hm, a common point K3 that belongs to the minus lateral edge Vm and the plus vertical edge Hp, and a common point K4 that belongs to de minus lateral edge Vm and the minus vertical edge Hm. For example, when the detected dark-bright edges correspond to the predetermined dark-bright edge patterns illustrated in FIGS. 12A through 12D, such edges are determined as the red-eye effect occurring pupil P. Further, when ratio of the existence of the detected dark-bright edges corresponding to the dark-bright edge pattern is equal to or more than the predetermined ratio, such detected dark-bright edges may be determined as the red-eye effect occurring pupil P.

Figure 12A:
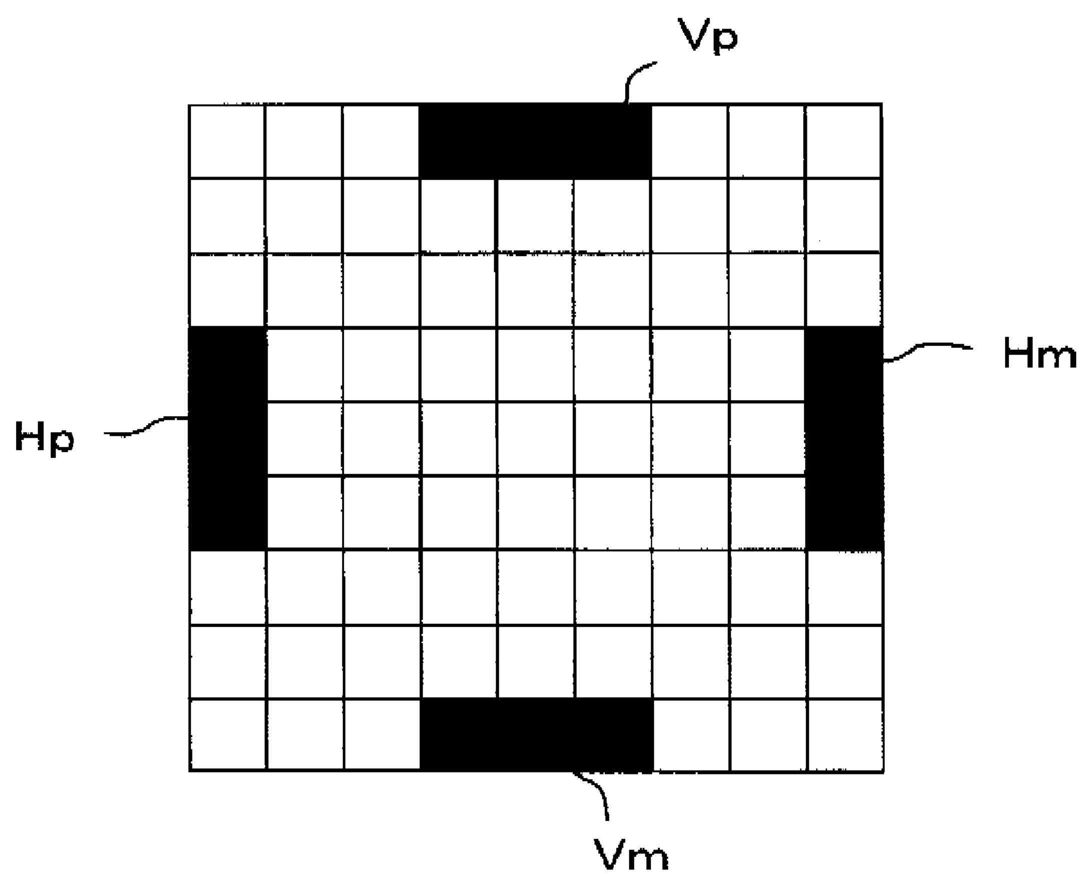
FIG. 12A illustrates an example of an edge pattern for detecting the red-eye effect.
Figure 12C:
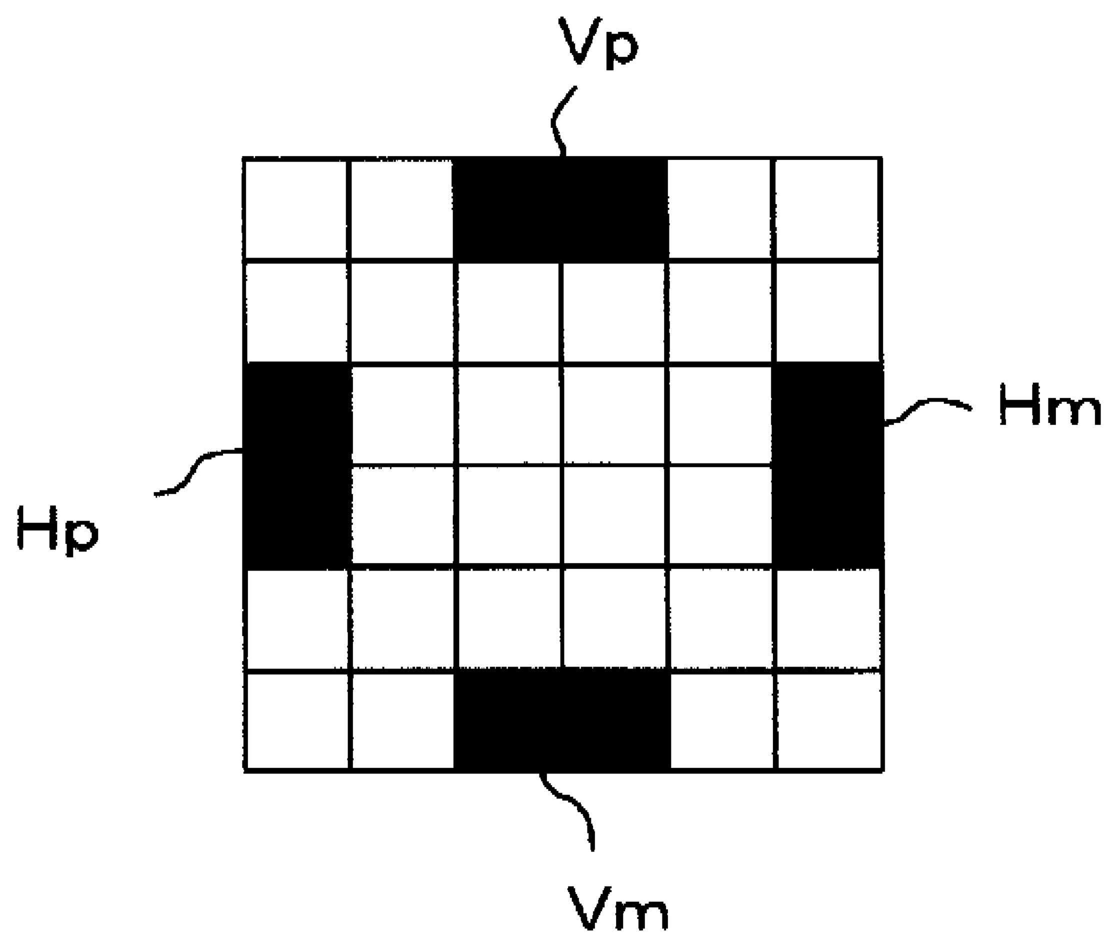
FIG. 12C illustrates an example of the edge pattern for detecting the red-eye effect.
Figure 12D:
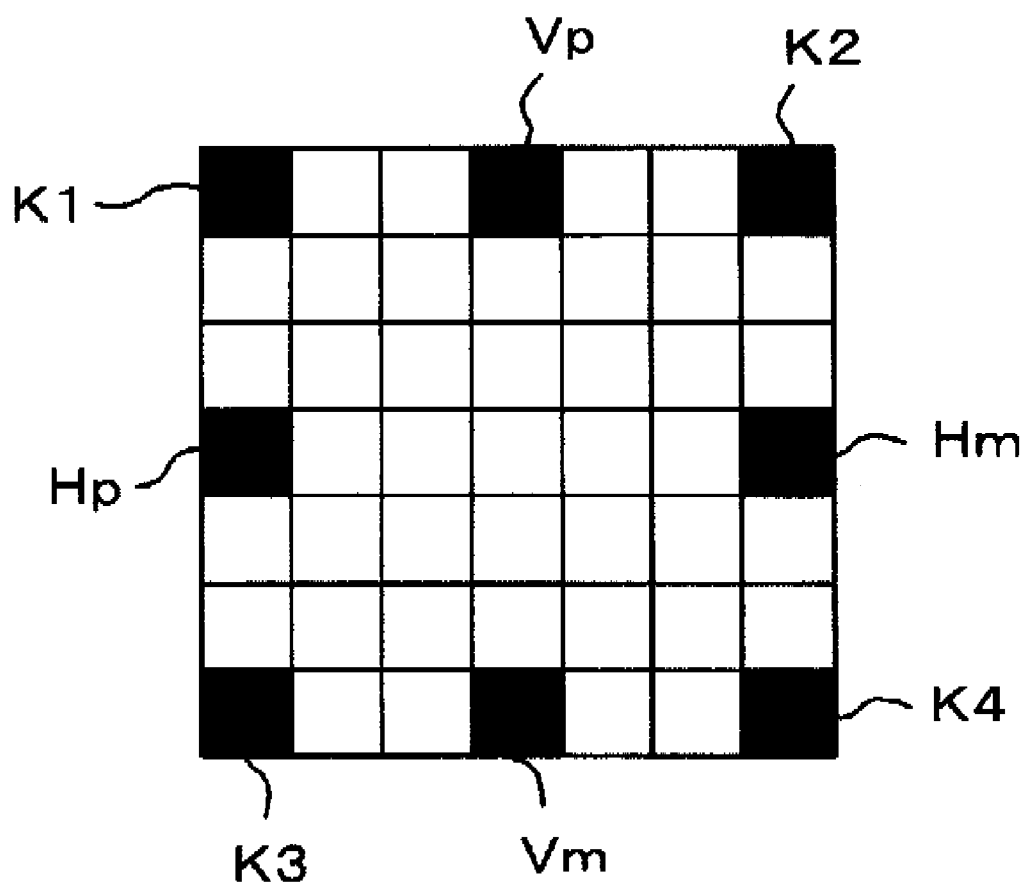
FIG. 12D illustrates an example of the edge pattern for detecting the red-eye effect.

Specifically, in FIGS. 12A through 12C, the detected dark-bright edges are determined as the red-eye effect occurring pupil P under conditions where a value indicating the level of the edge in the plus lateral edge Vp is larger than a predetermined threshold value A, a value indicating the level of We edge in the minus lateral edge Vm is smaller than a predetermined threshold value B, a value indicating the level of the edge in the plus vertical edge Hp is larger than a predetermined threshold value C, and a value indicating the level of the edge in the minus vertical edge X is smaller than a predetermined threshold value D. At this point, each value indicating the level of the edge includes a change value of the brightness or a value obtained by using the sobel filter, and such value will be referred to as an edge value.

In this example, because the patterns that are similar to the operators for detecting the edges illustrated in FIGS. 4A through 4B, brightness of the edge value changing from bright to dark in a direction from top to bottom or a direction from left to right is a plus edge value, and brightness of the edge value changing from dark to bright in a direction from top to bottom or a direction from left to right is a minus edge value.

Further, the threshold values A and C are plus values, and the threshold values B and D are minus values. Each threshold value A, B, C and D may have an identical absolute value or may have a different absolute value.

Further, as illustrated in FIG. 12D, each point K1 trough K4 commonly belonging to the vertical edge and the lateral edge is determined on the basis of a composite value of the vertical edge (horizontally changing edge) and the lateral edge (vertically changing edge).

Specifically, referring to the common point K1 in FIG. 12D, a value calculated by use of the sobel filter of a horizontally changing edge of a pixel is set to H, and a value calculated by use of the sobel filter of a vertically changing edge of the pixel is set to V, brightness of the common point K1 is determined to be high when the value obtained by adding H to V is larger than threshold value "c". In the same manner as the common point K1, brightness of the common point K2 is determined to be high when a value obtained by adding −H to V is larger than a threshold value K4, brightness of the common point K3 is determined to be high when a value obtained by adding H to −V is lager than a threshold value "e", and brightness of the common point K4 is determined to be high when a value obtained by adding −H to −V is larger than a threshold value "f". Each threshold value "c", "d", "e", and "f" may be the same value or may be the different value.

When the red-eye effect detecting portion 25 detects the red-eye effect, the position of the red-eye effect occurring pupil is set to the red-eye effect occurring pupil data 54, and the red-eye effect occurring pupil data 54 is memorized in the data storing portion 5. When the red-eye effect is not detected, the data storing portion 5 memorizes no red-eye effect.

When the red-eye effect is detected, the red-eye eliminating portion 26 eliminates the vertically changing edge existing at the upper and lower portions of the red-eye effect occurring pupils from the possible lower eyelids and the possible upper eyelids. In other words, the red-eye eliminating portion 26 ignores the vertically changing edge existing at the upper and lower portions of the red-eye effect occurring pupils so as not to be considered as the possible lower and upper eyelids. Specifically, because the red-eye effect occurring pupil corresponds to the dark-bright pixel pattern for detecting the red-eye effect, a position of the vertically changing edges appearing at the upper and lower portions of the red-eye effect occurring pupil has already been identified. Thus, when the dark-bright pixel pattern is placed on the red-eye effect occurring pupil, the possible eyelids existing at the border between the bright area and the dark area may be determined as the vertically changing edge of the red-eye effect occurring pupil.

The eyelid determining portion 27 determines a pair of the upper and lower eyelids by selecting a most appropriate pair of the upper and lower eyelids from remaining possible upper eyelids and possible lower eyelids. For example, the most appropriate pair of the upper and lower eyelids is determined when a length of the edge of the possible upper eyelid is approximately identical to a length of the edge of the possible lower eyelid, when a position of a central point of the edge of the possible upper eyelid is approximately identical to a position of a central point of the edge of the possible lower eyelid in a lateral direction, or when a distance between the central point of the edge of the possible upper eyelid and the central point of the edge of the possible lower eyelid is in a predetermined range of length.

Specifically, by setting the length of the edge of the possible upper eyelid to Lm, setting the length of the edge of the possible lower eyelid to Lp, and setting a threshold value to Lt, pairs of the possible upper and lower eyelids that fulfill a formula "$|Lm-Lp|<Lt$" remain as the candidates.

Further, by setting a X-coordinate of the center point of the edge of the possible upper eyelid to Xm, setting a X-coordinate of the center point of the edge of the possible lower eyelid to Xp, and setting a threshold value to Xt, pairs of the possible upper and lower eyelids that fulfill a formula "$|Xm-Xp|<Xt$" remain as the candidates.

Furthermore, by setting a Y-coordinate of the center point of the edge of the possible upper eyelid to Ym, setting a Y-coordinate of the center point of the edge of the possible lower eyelid is set to Yp, and setting a threshold value to Dt, pairs of the possible upper and lower eyelids that fulfill a formula "$(Xm-Xp)2+(Ym-Yp)2<Dt$" remain as the candidates.

From the remaining possible upper and lower eyelids, a most appropriate pair of upper and lower eyelids, which corresponds to a left or right eye, and whose position of the central point of the edge of the upper eyelid is most identical to the position of the central point of the edge of the lower eyelid, is selected. The selected pair of the upper and lower eyelids is memorized in the data storing portion 5 as an eyelid data.

The display processing portion 28 displays the selected pair of upper and lower eyelids on the display device 7 together with an outline of the face. On the basis of the pair of the upper and lower eyelids, an opening level of the eye may be determined. Further, an awaken level may be estimated on the basis of the opening level of the pair of the upper and lower eyelids. When it is determined that the driver is drowsing at the wheel, a waning with a sound may be displayed on the display device 7. Furthermore, a visual direction of the driver may be estimated on the basis of the data related to the pair of the upper and lower eyelids. The display device 7 may not be provided as a part of the eyelid detecting apparatus 1.

An operation of the eyelid detecting apparatus will be explained in detail. The operation of the eyelid detecting apparatus 1 is executed by the controlling portion 14 in cooperation with the camera 2, the sending and receiving portion 16, the image memory 12, the external memorizing portion 13 and the main memorizing portion 15.

Figure 11:
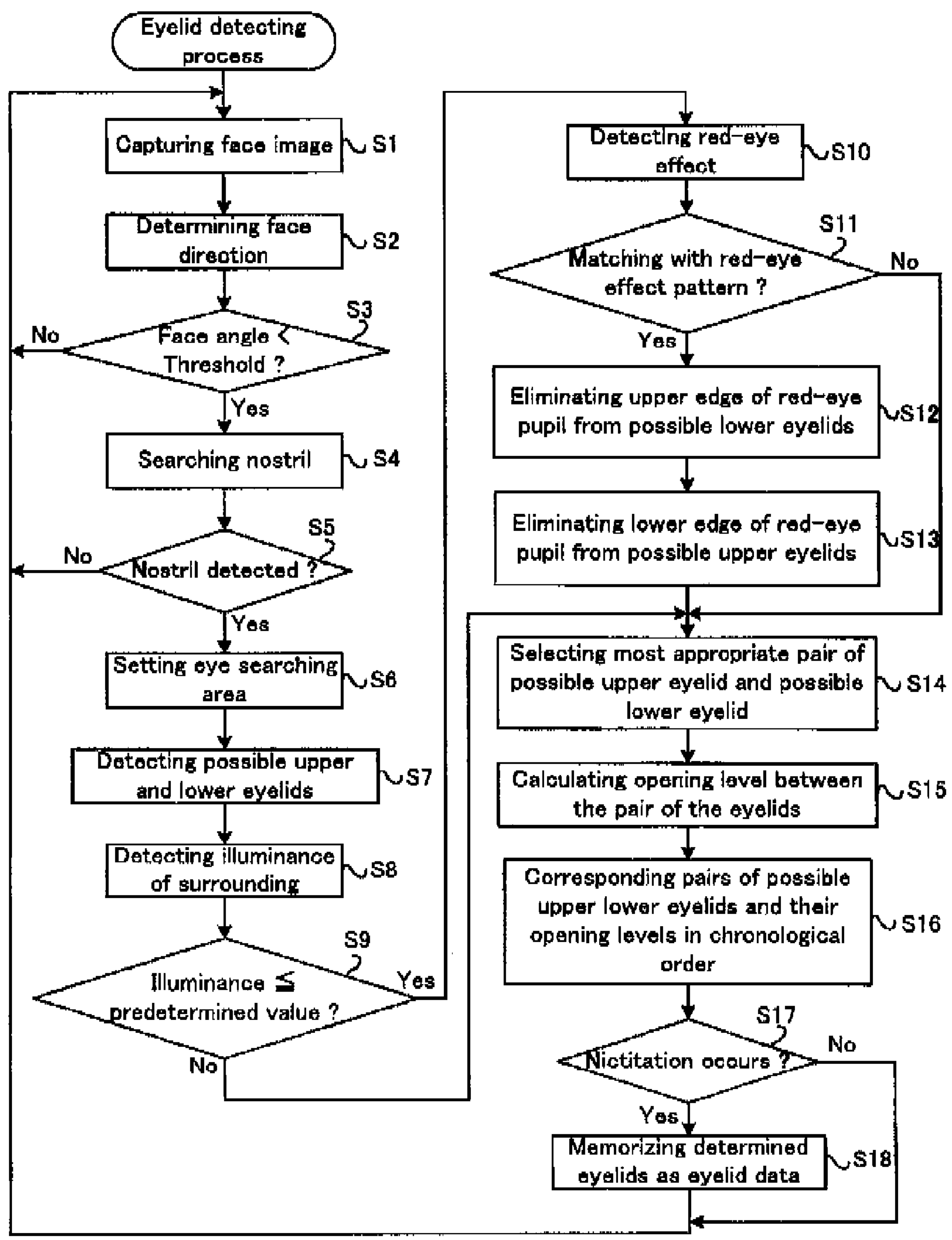
FIG. 11 illustrates a flowchart indicating an example of a process executed by the eyelid detecting apparatus.

FIG. 11 illustrates a flowchart indicating an example of the operation of the eyelid detecting apparatus 1. The controlling portion 14 inputs the face image captured by the camera 2 via the sending and receiving portion 16 in Step S1. Then, in Step S2, the face area is set, and a direction of the face is determined. The direction of the face is determined on the basis of a symmetric characteristic of the face line, and relative positions of the eyebrows and the chin. Then it is determined that the face direction is equal to or more than a predetermined angle (Step S3: No), because the face image is not appropriate for the eyelid detection, and the controlling portion 14 inputs a next frame of the face image (Return to Step S1).

When the face direction is equal to or less than the predetermined angle (Step S3: Yes), the nostril is searched (Step S4). If the nostril is not detected (Step S5: No), because the present image is not appropriate for the eyelid detection, the next face image is inputted (Step S1). If the nostril is detected (Step S5: Yes), the eyelid searching area is set in the face image (Step S6).

The controlling portion 14 computes a horizontally changing edge and a vertically changing edge within the eyelid searching area, which is set in the abovemetioned step, and the possible upper and lower eyelids are detected (Step S7). The controlling portion 14 groups the computed horizontally and vertically changing edges, and the edges that are equal to or less than a predetermined length (the number of continued points) are eliminated from the candidates. Further, a length and a central point of the edge are calculated. Further, likelihood of the possible upper eyelid and the possible lower eyelid may be calculated on the basis of shapes of the vertically changing edge and the horizontally changing edge and a positional relation between the vertically changing edge and the horizontally changing edge.

Then, the illuminance (brightness) of the surrounding is inputted from the illuminance sensor 4 (Step S8), and if the illuminance is equal to or less than a predetermined value (Step S9: Yes) the red-eye effect is detected (Step S10). On the other hand, if the illuminance is greater than the predetermined value (Step S9: No), the red-eye effect is not detected, and the controlling portion 14 proceeds to Step S14 and determines a most appropriate pair from the possible upper eyelids and the possible lower eyelids.

For example, the red-eye effect is detected by use of the dark-bright pixel pattern in Step S10. A partial image in the image that corresponds to any one of plural dark-bright pixel patterns may be set as the red-eye effect occurring pupil. If the red-eye effect is detected (Step S81: Yes), the upper edge of the red-eye effect occurring pupil is ignored so as not to be considered as the possible lower eyelids (Step S12), and the lower edge of the red-eye effect occurring pupil is ignored so as not to be considered as the possible upper eyelids (Step S13). If the red-eye effect is not detected (Step S11: No), the abovementioned eliminating processes are not executed.

As mentioned above, the most appropriate pair of the possible upper eyelid and the possible lower eyelid is selected from the remaining possible eyelids in Step S14.

In case where three or more pairs of possible eyelids remain, the appropriate pair of eyelids is determined on the basis of its nictitation. Further, in Step S15, the level of the opening between the pair of the eyelids is calculated. Specifically, the level of the opening indicates a distance between the central point of the upper eyelid and the central point of the lower eyelid.

The pairs of the possible upper lower eyelids and their opening levels correspond in chronological order (Step 16), and when it is considered that the change of the opening level is caused by the nictitation (Step S17: Yes), the pair of the upper and lower eyelids is determined as eyelids, and the determined eyelids are memorized as the eyelid detection data 55 (Step S18). For examples the pair of the possible upper lower eyelids, whose opening level is equal to or more than the predetermined value, changes its opening to be small and then changes to be large within a predetermined number of the frames, then it is determined that a nictitate occurs.

If the nictitate does not occur at the possible eyelids (Step S17: No), the possible eyelids are not determined as eyelids, and a next image is inputted (Step S1). Wile the eyelids detecting process is repeated, when the nictitate occurs, the eyelids are appropriately determined. When there are two possible eyelids, and when the eyelids are surely determined on the basis of their positions, shapes and positional relations, the eyelids do not need to be determined on the basis of their nictitate.

The opening level of the eyelids may be used for other processes. For example, when the opening level of the eyelids decreases within a continuous image of more than a predetermined number of the frame, the control portion 14 may determine that the driver is drowsing.

According to the eyelid detecting apparatus 1, even when the red-eye effect occurs, the eyelids are appropriately detected in the face image data.

The above-mentioned hardware configuration and the processes illustrated in the flowcharts describe only an example of the configuration and operations of the eyelid detecting apparatus 1, and any desired changes and modifications may be applied.

The control device 14, the sending and receiving portion 16, the image memory 12, the external memorizing portion 13, the main memorizing portion 15 and the like mainly execute the processes in the eyelid detecting apparatus 1. Each of the parts mainly executing the processes may not be specialized for the processes, instead, a general used computing system may be employed. For example, a computing program for executing the above-mentioned operations stored in a readable storage media, such as a flexible disc, the CD-ROM, DVD-ROM and the like is installed in a computer, and such computer may be used for executing the above-mentioned processes in the same manner as the eyelid detecting apparatus 1. Further, the computing program is uploaded to a memory device of a server device, which is connected to a communication network such as the internet and the like, then the computer that is able to access the communication network downloads and installs the computing program, and such computer may be used for executing the above-mentioned processes in the same manner as the eyelid detecting apparatus 1.

The computer is run by an operating system (OS) and an application program. In a case where the processes are executed by the computer in the same manner as the eyelid detecting apparatus 1 by the OS and the application program respectively, or by in cooperation with the OS and the application program, only the application program may be stored in the storage media or the memory device.

Additionally, the computing system may be delivered through the communication network by overlapping the computing program on a carrier wave. For example, the computing program may be uploaded to a bulletin board system (BBS) in the communication network so that the computing program is downloaded through the network to each computer. Then, the above-mentioned processes may be executed by executing the computing program, which is installed in the computer, together with other application program under the control of the OS.

Thus, according to the eyelid detecting apparatus, an eyelid may be accurately detected even when the red-eye effect occurs in the face image.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

The invention claimed is:

1. An eyelid detecting apparatus comprising:

an image capturing means for capturing a face image;

a red-eye effect detecting means for detecting a red-eye effect in which a light appears red at the pupil in the face image, the light entering through the pupil, reflecting on a choroidea of the eye, and exiting from the pupil; and an eyelid detecting means for detecting an upper eyelid and a lower eyelid in the face image on the basis of an edge appearing on a boundary between a bright portion and a dark portion; and the eyelid detecting means ignoring the edge of a red-eye effect occurring pupil so as not to be considered as the upper eyelid and the lower eyelid when the red-eye effect detecting means detects the red-eye effect, wherein the eyelid detecting means includes a possible eyelid detecting means for detecting a possible upper eyelid and a possible lower eyelid on the basis of the edge appearing on the boundary between the bright portion and the dark portion, wherein the eyelid detecting means ignores the edge of the red-eye effect occurring pupil so as not to be considered as the possible upper eyelid and the possible lower eyelid when the red-eye effect detecting means detects the red-eye effect.

2. The eyelid detecting apparatus according to claim 1, wherein the eyelid detecting means ignores an upper edge of a red-eye effect occurring pupil so as not to be considered as the lower eyelid when the red-eye effect detecting means detects the red-eye effect.

3. The eyelid detecting apparatus according to claim 1, wherein the eyelid detecting means ignores a lower edge of the red-eye effect occurring pupil so as not to be considered as the upper eyelid when the red-eye effect detecting means detects the red-eye effect.

4. The eyelid detecting apparatus according to claim 1, wherein the red-eye effect detecting means detects a partial image in the face image as the red-eye effect occurring pupil, the partial image corresponding to a predetermined dark-bright pixel pattern.

5. The eyelid detecting apparatus according to claim 4, wherein the dark-bright pixel pattern includes a bright area at a central portion thereof and a dark area around the bright area.

6. The eyelid detecting apparatus according to claim 4, wherein the red-eye effect detecting means detects the partial image in the face image as the red-eye effect occurring pupil, the partial image corresponding to one of plural predetermined dark-bright pixel patterns, each of which has a different pattern.

7. The eyelid detecting apparatus according to claim 1, wherein the red-eye effect detecting means detects the partial image in the face image as the red-eye effect occurring pupil, the partial image including the edge whose shape fulfills a predetermined condition, the edge appearing on the boundary between the bright portion and the dark portion.

8. The eyelid detecting apparatus according to claim 1 further including an illuminance detecting means for detecting a level of brightness of surroundings and a red-eye effect detection execution determining means for determining whether or not the red-eye effect detection is executed by the red-eye effect detecting means on the basis of the level of brightness of the surroundings.

9. The eyelid detecting apparatus according to claim 8, wherein the red-eye effect detection execution determining means determines that the red-eye effect detection is not executed by the red-eye effect detecting means when the level of brightness of the surroundings is higher than a predetermined value.

10. The eyelid detecting apparatus according to claim 8, wherein the red-eye effect detection execution determining means determines that the red-eye effect detection is executed by the red-eye effect detecting means when the level of brightness of the surroundings is lower than a predetermined value.

11. A method of detecting red-eye effect comprising:

detecting a red-eye effect in which a light appears red at the pupil in the face image, the light entering through the pupil, reflecting on a choroidea of the eye, and exiting from the pupil;

detecting an upper eyelid and a lower eyelid in the face image on the basis of an edge appearing on a boundary between a bright portion and a dark portion; and ignoring the edge of a red-eye effect occurring pupil so as not to be considered as the upper eyelid and the lower eyelid when detecting the red-eye effect, wherein the detecting the upper eyelid and the lower eyelid comprises detecting a possible upper eyelid and a possible lower eyelid on the basis of the edge appearing on the boundary between the bright portion and the dark portion, and wherein the ignoring comprises ignoring the edge of the red-eye effect occurring pupil so as not to be considered as the possible upper eyelid and the possible lower eyelid when detecting the red-eye effect.

12. A computer-readable medium having embodied thereon a program which, when executed by a computer, causes the computer to function as:

a red-eye effect detecting means for detecting a red-eye effect in which a light appears red at the pupil in a face image, the light entering through the pupil, reflecting on a choroidea of the eye, and exiting from the pupil; and an eyelid detecting means for detecting an upper eyelid and a lower eyelid in the face image on the basis of an edge appearing on a boundary between a bright portion and a dark portion in a manner where the edge of a red-eye effect occurring pupil is ignored so as not to be considered as the upper eyelid and the lower eyelid when the red-eye effect detecting means detects the red-eye effect, wherein the eyelid detecting means includes a possible eyelid detecting means for detecting a possible upper eyelid and a possible lower eyelid on the basis of the edge appearing on the boundary between the bright portion and the dark portion, wherein the eyelid detecting means ignores the edge of the red-eye effect occurring pupil so as not to be considered as the possible upper eyelid and the possible lower eyelid when the red-eye effect detecting means detects the red-eye effect.

* * * * *